(12) United States Patent
Hyatt

(10) Patent No.: US 6,191,300 B1
(45) Date of Patent: Feb. 20, 2001

(54) PROCESS FOR THE PREPARATION OF CYCLOPROPYLACETONITRILE

(75) Inventor: John Anthony Hyatt, Kingsport, TN (US)

(73) Assignee: Eastman Chemical Company, Kingsport, TN (US)

( * ) Notice: Under 35 U.S.C. 154(b), the term of this patent shall be extended for 0 days.

(21) Appl. No.: 09/293,371

(22) Filed: Apr. 16, 1999

(51) Int. Cl.$^7$ ............................................. C07C 253/111
(52) U.S. Cl. ............................................................. 558/344
(58) Field of Search .................................................. 558/344

(56) References Cited

U.S. PATENT DOCUMENTS

| | | | | |
|---|---|---|---|---|
| 3,454,575 | * | 7/1969 | Mizzoni et al. | 260/256.4 |
| 4,144,269 | | 3/1979 | Klenk et al. | |
| 5,475,151 | | 12/1995 | Liang et al. | |
| 5,502,257 | | 3/1996 | Liang et al. | |

FOREIGN PATENT DOCUMENTS

| | | |
|---|---|---|
| 0 858 988 A1 | 8/1998 | (EP) . |
| 0 887 344 A1 | 12/1998 | (EP) . |
| 1336883 | 11/1973 | (GB) . |
| 07/173169 | 7/1994 | (JP) . |
| WO 98/09961 | 3/1998 | (WO) . |
| WO 98/34915 | 8/1998 | (WO) . |

OTHER PUBLICATIONS

Cartier and Bunce, J. Am. Chem. Soc., 85, 933–37 (1963).
Hanak and Ensslin, Annalen, 697, 100–10 (1966).
Mizzoni et al., J. Med. Chem., 13, 878–82 (1970).
Pardo and Morize, JCS Chem. Comm., 1037–39 (1982).
Roberts and Mazur, J. Am. Chem. Soc., 73, 2509–20 (1951).
Hrubiec and Smith, J. Org. Chem., 49, 431–35 (1984).
DuPont et al., Syn. Comm., 20 (7), 1011–21, 1990.
Carney and Wojtkunski, Org. Prep. Proceed. Int., 5 (1), 25–29 (1973).
Ueno et al., J. Med. Chem., 34, 2468–73 (1991).
Li et al., J. Med. Chem., 39, 3070–88 (1996).
Janusz et al., J. Med. Chem., 41, 3515–29 (1998).
Dakkouri and Kehrer Chem. Ber., 114, 3460–61 (1981).
Dehmlow and Dehmlow, Phase Transfer Catalysis, $2^{nd}$ ed., 42–49, 52–62, 82–86, Verlag Chemie, Deerfield, Beach, FL 1983.
Fenick, David J., et al, *Journal of Organic Chemistry*, 1994, pp. 4791–4799, vol. 59, No. 17, U.S.

* cited by examiner

Primary Examiner—Cecilia Tsang
Assistant Examiner—Joseph Murray
(74) Attorney, Agent, or Firm—Michael J. Blake; Harry J. Gwinnell

(57) ABSTRACT

Disclosed is a process for the preparation and recovery of cyclopropylacetonitrile by a novel combination of process steps beginning with a mixture of cyclopropylmethyl halide, a cyclobutyl halide and a 4-halo-1-butene. The process permits the recovery of substantially pure cyclopropylacetonitrile and cyclobutyl halide, e.g., cyclopropylacetonitrile and cyclobutyl halide each having a purity greater than about 95%.

5 Claims, No Drawings

PROCESS FOR THE PREPARATION OF CYCLOPROPYLACETONITRILE

This invention pertains to the preparation of cyclopropylacetonitrile by reacting a cyclopropylmethyl halide with a cyanide reactant. More specifically, this invention pertains to a novel combination of process steps for the preparation and recovery of cyclopropylacetonitrile beginning with a mixture of cyclopropylmethyl halide, a cyclobutyl halide and a 4-halo-1-butene. The process permits the recovery of substantially pure cyclopropylacetonitrile and cyclobutyl halide, e.g., cyclopropylacetonitrile and cyclobutyl halide each having a purity greater than about 95%.

BACKGROUND

Previous attempts to prepare cyclopropylacetonitrile have proceeded via cyanide displacement of the intermediate cyclopropylmethyl bromide or cyclopropylmethyl chloride. For example, Cartier and Bunce, *J. Am. Chem. Soc.*, 85, 935 (1963) reacted cyclopropylmethyl bromide with sodium cyanide in ethanol and isolated pure cyclopropylacetonitrile in 20% yield using preparative gas chromatography. Hanak and Ensslin, *Annalen*, 697, 100 (1966) carried out the same reaction and reported a yield of 24%; cyclopropylmethyl chloride gave a yield of only 15%. A substantial improvement is described by Mezzoni et al., *J. Med. Chem.*, 13, 878 (1970) wherein the reaction of cyclopropylmethyl bromide with sodium cyanide in dimethylsulfoxide at 70° C. gave, after a cumbersome workup, a 76% yield of cyclopropylacetonitrile. Finally, Pardo and Morize, *JCS Chem. Comm.*, 1982, 1037, mention, in a communication devoid of experimental data or reaction conditions, that cyclopropylacetonitrile was obtained from cyclopropylmethyl bromide in 75% yield using "phase-transfer".

Cyclopropylmethyl halide, from which the desired cyclopropylacetonitrile may be obtained, can be prepared from cyclopropanemethanol. The simplest process for preparing cyclopropylmethyl halide comprises contacting cyclopropane methanol with an aqueous hydrogen halide solution. However, this process gives a product which comprises a cyclobutyl halide (e.g., cyclobutyl bromide b.p.=108° C.) and a 4-halo-1-butene (e.g., bromobutene b.p.=100° C.) in addition to the desired cyclopropylmethyl halide (e.g., cyclopropylmethyl bromide b.p.=1 06° C.). See, for example, Roberts and Mazur, *J. Am. Chem. Soc.*, 72, 2509 (1951). These by-products are very difficult to separate by distillation, a problem exacerbated by the formation of azeotropes of cyclopropylmethyl halide, cyclobutyl halide, and 4-halo-1-butene with common organic solvents. Thus, Cartier and Bunce (vide supra) reacted cyclopropane methanol with $PBr_3$ at −20° C. to give cyclopropylmethyl bromide contaminated with cyclobutyl bromide and bromobutene. Other workers have avoided the contamination and separation problems by using more selective reagents for converting cyclopropane methanol to cyclopropylmethyl halide. For example, Mitani et al., European Patent Application EP 0 858 988 A1 convert cyclopropane methanol to an intermediate sulfonate ester which is then displaced with bromide ion to give cyclopropylmethyl bromide in good yield and purity. Hrubiec and Smith, *J. Org. Chem.*, 49, 431 (1984) used bromine in the presence of triphenylphosphine and dimethylformamide to transform cyclopropane methanol into cyclopropylmethyl bromide. It is apparent that all of these methods for the synthesis of cyclopropylmethyl halide suffer from the need for difficult separations, use intermediate compounds such as sulfonates, or generate wastes which are difficult to handle, e.g., triphenylphosphine oxide.

However, the preferred method for preparing cyclopropylmethyl halide for use in producing the subject nitrile would be the reaction of cyclopropane methanol with aqueous hydrogen halide, if the problem of isomer separation could be overcome. As in the case of halide compounds cyclopropylmethyl halide, cyclobutyl halide, and 4-halo-1-butene, the nitrile (or cyano) compounds corresponding to cyclopropylmethyl halide, cyclobutyl halide, and 4-halo-1-butene also are virtually impossible to separate on a commercial scale.

Cyclobutyl halide of acceptable purity also is difficult to obtain. As mentioned above, reaction of the alcohol (i.e., cyclopropane methanol) with aqueous hydrogen halide leads, through rearrangement chemistry, to an appreciable amount of cyclobutyl halide. However, cyclobutyl halide cannot be separated on commercial scale from the co-produced cyclopropylmethyl halide and 4-halo-1-butene. Pure cyclobutyl halide apparently is best prepared by a multistep procedure proceeding via a Hunsdiecker reaction of cyclobutanecarboxylic acid (DuPont et al., *Syn. Comm.*, 20, 1011 (1990)). This process affords cyclobutyl halide contaminated by a 5–8% of cyclopropylmethyl halide and uses stoichiometric amounts of expensive silver nitrate reagent and toxic carbon tetrachloride solvent.

BRIEF SUMMARY OF THE INVENTION

I have developed a process for the preparation of cyclopropyl-acetonitrile in a purity of at least 90 weight percent, preferably at least 95 weight percent, from a halide mixture comprising cyclopropylmethyl halide, cyclobutyl halide and 4-halo-1-butene, which, as mentioned hereinabove, may be readily obtained by the reaction of cyclopropanemethanol with aqueous hydrogen halide. The process also can be utilized to recover cyclobutyl halide in a purity of at least 90 weight percent, preferably at least 95 weight percent. The first embodiment of the present invention provides a process for the preparation of cyclopropylacetonitrile by the steps comprising:

(1) contacting a reactant mixture comprising a cyclopropylmethyl halide, a cyclobutyl halide and a 4-halo-1-butene with an aqueous solution of an alkali metal cyanide in the presence of a phase transfer catalyst to obtain a reaction mixture comprising (i) an organic phase comprising cyclopropylacetonitrile, cyclobutyl halide, 1-cyano-3-butene and phase transfer catalyst and (ii) an aqueous phase comprising a solution of the alkali metal halide and cyanide and phase transfer catalyst;

(2) separating organic phase (i) from aqueous phase (ii) from step (1);

(3) contacting organic phase (i) from step (2) with elemental halogen to obtain a reaction mixture comprising cyclopropylacetonitrile, cyclobutyl halide, 4-cyano-1,2-butane dihalide and phase transfer catalyst; and (4) subjecting the reaction mixture of step (3) to fractional distillation to obtain overhead vapor products comprising cyclopropylacetonitrile and cyclobutyl halide and a distillation base residues comprising 4-cyano-1,2-butane dihalide and phase transfer catalyst.

As those skilled in the art will recognize, best results are obtained when the halides and elemental halogen used in the process are bromides and bromine.

Cyclopropylacetonitrile and cyclobutyl halides are useful chemical intermediates in the preparation of valuable fine chemicals and pharmaceuticals. The utility of cyclopropylacetonitrile is illustrated by the work of Carney and Wojtkunski, *Org. Prep. Proceed. Int*, 5, 25 (1973), Ueno et al., *J. Med. Chem.*, 34, 2468 (1991), Li et al., *J. Med. Chem.*, 39, 3070 (1996), and Janusz et al., *J. Med. Chem.*, 41, 3515 (1998). Cyclobutyl halide likewise is shown to be useful by reference to the work of Fox et al., Published European Patent Application EP 887344 A1 981230, Robinson, PCT Application WO 98/34915 A1 980813), Marfat, PCT Appication WO 98/09961 A1 980312, Myake and Nakao Japanese Kokai JP 07/173169 A2 950711, and Dakkouri and Kehrer Chem. Ber., 114, 3460 (1981).

DETAILED DESCRIPTION

In the first step of the process, a mixture of cyclopropylmethyl halide, cyclobutyl halide, and 4-halo-1-butene is contacted with an aqueous solution of an alkali metal cyanide, e.g., sodium and/or potassium cyanide, in the presence of a phase-transfer catalyst. This step is carried out under reaction conditions which results in the conversion of the mixture of cyclopropylmethyl halide, cyclobutyl halide, and 4-halo-1-butene into a mixture of cyclopropylacetonitrile (b.p.=148° C.), cyclobutyl halide (e.g., cyclobutyl bromide b.p.=108° C.) and 1-cyano-3-butene (b.p.=140° C.). This is best done by stirring the mixture of cyclopropylmethyl halide, cyclobutyl halide, and 4-halo-1-butene with at least 0.6 moles, preferably about 1.2 to 3 moles, most preferably about 1.5 moles of alkali metal cyanide per mole of each of halide reactants cyclopropylmethyl halide, cyclobutyl halide, and 4-halo-1-butene. The use of lower amounts of cyanide requires very long reaction times whereas reactions are quicker at the upper end of the cyanide range, but the excess cyanide is wasted and is a disposal problem. The aqueous solution of alkali metal cyanide may contain from about 5 up to 50 weight percent, preferably about 27 to 37 weight percent, alkali metal hydroxide. The alkali metal cyanide preferably is sodium or potassium cyanide.

Operation of the first step at temperatures at and above about 80° C. gives significant cyanide displacement of the cyclobutyl bromide leading to formation of cyclobutyl cyanide which is inseparable from the cyclopropylacetonitrile. Furthermore, at reaction temperatures much above 60° C., the reaction mixture tends to discolor significantly and form tarry by-products which lead to reduced yields. Therefore, the selective cyanide displacement reaction normally is carried out at a temperature of less than 60° C. and preferably at a temperature of about 35.to 55° C.

The choice of phase transfer catalyst is not critical and most commonly-used ones are effective. For a discussion of such catalysts, see Dehmlow and Dehmlow, *Phase Transfer Catalysis*, $2^{nd}$ ed., Verlag Chemie, Deerfield Beach, Fla., 1983. In general, quaternary ammonium and phosphonium salts, e.g., halides and hydrogen sulfates, and hydroxides containing a total of about 8 to 64 carbon atoms, preferably about 10 to 36 or more carbon atoms perform well. These include tetrabutylammonium hydrogen sulfate, tetrabutyl ammonium bromide, tricapryl(methyl)-ammonium chloride (available under the tradename "Aliquat 336"), benzyl (trimethyl)ammonium chloride, bromide, iodide, or hydroxide, tributylhexadecylphosphonium bromide, ethyl (triphenyl)phosphonium bromide, tetrabutylphosphonium chloride, and the like. Certain nonionic phase transfer catalysts are known and also may be used in the cyanide displacement step. Examples of such nonionic phase transfer catalysts include crown ethers such as 18-crown-6, dicyclohexyl-18-crown-6, and the like, and also certain polymeric catalysts such as poly(ethylene glycol) and its ethers. These catalysts and many other suitable ones are discussed by the cited Dehmlow and Dehmlow publication.

Preferred phase transfer catalysts contain about 12 to 36 carbon atoms and have the general formula:

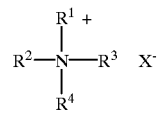

wherein $R^1$, $R^2$, $R^3$, and $R^4$ are the same or different and are selected from alkyl of up to about 18 carbon atoms and benzyl and X is an anion, e.g. Cl, Br, I, F, HSO4, OH, etc.

The amount of catalyst should be chosen so as to give a convenient reaction time and temperature. Thus, very low amounts of catalyst will lead to slow reactions, and attempts to counteract this by raising the temperature will lead to problems such as non-selective reactions and/or decomposition. Thus, the amount of catalyst employed should give a reasonable reaction rate at temperatures below about 60° C., and preferably in the range of 40 to 55° C. Normally, the amount of phase transfer catalyst employed will be in the range of about 5 to 20 weight percent, preferably about 7 to 17 weight percent, based on the total weight of reactants cyclopropylmethyl halide, cyclobutyl halide, and 4-halo-1-butene. Tricapryl(methyl)ammonium chloride employed in a concentration of about 7 to 17, preferably 11 to 13, weight percent (same basis) is a particularly effective catalyst.

The mixture of cyclopropylmethyl halide, cyclobutyl halide, and 4-halo-1-butene used in the first step may be prepared by contacting cyclopropanemethanol with an aqueous hydrogen halide solution at a temperature in the range of about −20° to 35° C. The reaction is mildly exothermic and, thus, it is preferably conducted at a temperature between about −5 and 10° C. The reaction time is dictated by the temperature and by the time necessary for the product to separate from the initially homogeneous mixture. In the temperature range of −5 to 10° C., a time of at least 4 hours, but not more than 24 hours, normally is required. A reaction period of about 12 to 14 hours at 5° C. has been found to give good results.

The concentration of the aqueous hydrogen halide solution may be in the range of about 20 to 48 weight percent hydrogen halide, preferably about 30 to 48 weight percent hydrogen halide. The hydrogen halide preferably is hydrogen bromide which may be provided in the form of an aqueous solution containing about 30 to 48 weight percent HBr. The amount of hydrogen halide used relative to the alcohol determines to a large degree the yield of the reaction. For example, a fourfold molar excess of HBr yields about 80% of the theoretically possible amount of cyclopropylmethyl halide, cyclobutyl halide, and 4-halo-1-butene. Smaller amounts give proportionally lower yields, with a twofold excess yielding only about 40% of theory. The use of 48% aqueous HBr in a 3.5 to 5-fold excess with respect to the cyclopropanemethanol reactant has been found to give good results.

The reaction of cyclopropane methanol with the aqueous hydrogen halide results in the formation of a two-phase liquid system comprising an organic phase comprising halide products cyclopropylmethyl halide, cyclobutyl halide and 4-halo-1-butene and an aqueous phase comprising the aqueous hydrogen halide solution. The crude product thus can be recovered by decantation. The relative weights of halide products cyclopropylmethyl halide, cyclobutyl halide and 4-halo-1-butene, based on the total weight of cyclopropylmethyl halide, cyclobutyl halide and 4-halo-1-butene= 100%, typically are in the range of about 40 to 60% cyclopropylmethyl halide, about 30 to 50% cyclobutyl halide and about 5 to 10% 4-halo-1-butene.

Cyclopropanemethanol utilized in the preparation of halides cyclopropylmethyl halide, cyclobutyl halide and 4-halo-1-butene is readily obtained by the hydrogenation of cyclopropanecarbox-aldehyde (CPCA) in the presence of a cobalt or nickel catalyst according to the process described in U.S. Pat. No. 5,475,151. The CPCA may be produced by the thermal isomerization of 2,3-dihydro-furan as is described in U.S. Pat. No. 5,502,257.

Although distillative separation of the nitrile from cyclobutyl bromide is simple, the presence of a low level of the butenyl nitrile, 1-cyano-3-butene, poses a problem. While a very efficient distillation will separate cyclopropylacetonitrile from 1-cyano-3-butene, the separation is much easier if elemental halogen is added to the crude product of the cyanide displacement reaction to selectively transform 1-cyano-3-butene into 1-cyano-3,4-dibromobutane. Therefore, step 3 of the process of the present invention involves contacting the organic phase of step 1 comprising a mixture of cyclopropylacetonitrile, cyclobutyl halide, and 1-cyano-3-butene with sufficient elemental halogen, e.g., chlorine or, preferably, bromine, to convert 1-cyano-3-butene to 1-cyano-3,4-dibromobutane. The amount of halogen added to the organic phase of step 1 normally is at least 1 mole, preferably about 1 to 1.2 moles, halogen per mole of 1-cyano-3-butene present. Step 3 may be carried out at a temperature of about −10 to 30° C., preferably about 10 to 25° C.

Step 4 of the present process involves fractional distillation of the product mixture from step 3 to obtain overhead vapor products comprising substantially pure cyclopropylacetonitrile and/or cyclobutyl halide and a distillation base residues comprising 4-cyano-1,2-butane dihalide and phase transfer catalyst. The distillation preferably is carried out in the presence of an acid scavenger to prevent hydrogen halide corrosion and contamination of the distillates and/or to conduct the distillation at reduced pressure, e.g., pressures as low as 50 Torr, preferably at pressures in the range of about 50 to 100 Torr, and hence lower temperature at which hydrogen halide formation is minimized. Examples of acid scavengers which may be employed in the distillation include organic amines such as trialkylamines, triethanolamine, pyridine and the like, amides such as N-methylpyrrolidone and N-cyclohexylpyrrolidone, and/or inorganic bases such as sodium or potassium bicarbonate, sodium or potassium carbonates, and carboxylate salts of strong bases e.g., sodium acetate. The preferred acid scavengers are the trialkylamines, including trialkanolamines, having boiling points greater than the boiling point of any of the components of the crude product being distilled, e.g., trialkylamines having boiling points of about 100 to 250° C. at ambient pressure. The amount of acid scavenger typically required gives an acid scavenger:crude product weight ratio in the range of about 0.001:1 to 0.1:1.

The process of this invention can, in principle, be carried out utilizing either bromide or chloride compounds. However, the use of the less reactive chlorides necessitates a higher temperature in the phase-transfer cyanide displacement reaction and results in the formation of dark and tarry by-products which leads to difficult isolation and lowered yield of products. Therefore the use of bromides is preferred to that of chlorides.

The process provided by the present invention is further illustrated by the following examples. Gas chromatographic (GC) analyses were performed on a Hewlett-Packard 5890 series 11 gas chromatography with a 30 meter DB-Wax and a 30 meter DB-17 capillary columns. The identities of the products obtained were confirmed by nuclear magnetic spectrometry and gas chromatography-mass spectrometry by comparison to authentic samples. The percentages specified in the examples are by weight unless otherwise specified.

Step 1

A flask was equipped with stirrer, reflux condenser, thermometer, and charged with 75 ml of water and 36.8 grams (0.75 mole) sodium cyanide. Stirring was commenced and there was added 8.5 grams of tricapryl(methyl) ammonium chloride (ALIQUAT 336 phase-transfer catalyst) followed by 67.5 grams (0.50 mole) of the bromide product mixture comprising 55.7% cyclopropylmethyl bromide, 37.2% bromocyclobutane, and 7.1% bromobutene. The mixture slowly exothermed to about 50° C. After about 1 hour, heating was commenced so as to maintain the temperature of the mixture at 45° C. After 7 hours, gas chromatographic analysis of the organic phase indicated that cyclopropylmethyl bromide and 4-bromo-1-butene (i.e., bromobutene) were consumed, that cyclobutyl bromide was unchanged, and that cyclopropylacetonitrile and 1-cyano-3-butene were formed. The ratio (area %) of cyclopropylacetonitrile to 1-cyano-3-butene was 88:12. A minute trace (less than 1 area %) of cyanocyclobutane was detected.

The bromide product mixture used in Step 1 was prepared by the following procedure: A 2-liter flask was charged with 1350 grams (912 ml, 8.1 moles) of 48% aqueous HBr. The HBr was cooled with stirring and there was added over a 1-hour period 140 grams (2 moles) of cyclopropanemethanol at 5–10° C. The initially clear mixture began to phase separate by the end of the addition. The mixture was stirred an additional hour, then stirring was stopped and the mixture was allowed to stand at 5° C. for 16 hours. The resulting lower product phase was drawn off, washed with water twice, and analysed by gas chromatography and NMR spectroscopy. These analyses agreed that the composition of the product was 7.1% bromobutene, 37.2% bromocyclobutane, and 55.7% cyclopropylmethyl bromide. Yield: 216 grams (82%). This product was used in Step 1 without further treatment.

Steps 2 and 3

The organic phase from Step 1 was separated, washed twice with brine, and cooled to 10° C. with stirring. Bromine, 8.8 grams (2.8 ml, 0.055 mole) was added dropwise over 20 minutes. After an additional 30 minutes at 22° C., gas chromatographic analysis indicated that only a barely detectable amount of 1-cyano-3-butene remained. The bromocyclobutane and cyclopropylacetonitrile were unchanged.

Step 4

The crude product was distilled through a 40.6 cm (16 inch) column packed with glass rings. Distillation of the product at 90 Torr using a reflux ratio of approximately 8:1 afforded water-wet bromocyclobutane at b.p. 43–48° C. After drying, the bromocyclobutane product weighed 17.7 grams (79% of theory). Further distillation at 25–30 Torr gave cyclopropyl-acetonitrile at bp 45–50° C.; yield: 18.7 grams (84% of theory). Both products had gas chromatographic retention times and nmr spectra in excellent accord with authentic samples.

The invention has been described in detail with particular reference to preferred embodiments thereof, but it will be understood that variations and modifications can be effected within the spirit and scope of the invention.

I claim:

1. Process for the preparation of cyclopropylacetonitrile by the steps comprising:
   (1) contacting a reactant mixture comprising a cyclopropylmethyl halide, a cyclobutyl halide and a 4-halo-1-butene with an aqueous solution of an alkali metal cyanide in the presence of a phase transfer catalyst to obtain a reaction mixture comprising (i) an organic phase comprising cyclopropylacetonitrile, cyclobutyl halide, 1-cyano-3-butene and phase transfer catalyst and (ii) an aqueous phase comprising a solution of the alkali metal halide and cyanide and phase transfer catalyst;
   (2) separating organic phase (i) from aqueous phase (ii) from step (1);
   (3) contacting organic phase (i) from step (2) with elemental halogen to obtain a reaction mixture comprising cyclopropylacetonitrile, cyclobutyl halide, 4-cyano-1,2-butane dihalide and phase transfer catalyst; and
   (4) subjecting the reaction mixture of step (3) to fractional distillation to obtain overhead vapor products comprising cyclopropylacetonitrile and cyclobutyl halide and a distillation base residues comprising 4-cyano-1,2-butane dihalide and phase transfer catalyst.

2. The process according to claim 1 wherein the reactant mixture employed in Step 1 comprises, based on the total weight of cyclopropylmethyl halide, cyclobutyl halide and 4-halo-1-butene=100%, about 40 to 60% cyclopropylmethyl halide, about 30 to 50% cyclobutyl halide and about 5 to 10% 4-halo-1-butene.

3. A process for the preparation of cyclopropylacetonitrile by the steps comprising:
   (1) contacting a reactant mixture comprising cyclopropylmethyl bromide, cyclobutyl bromide and 4-bromo-1-butene (bromobutene) with an aqueous solution of an alkali metal cyanide in the presence of a phase transfer catalyst to obtain a reaction mixture comprising (i) an organic phase comprising cyclopropylacetonitrile, cyclobutyl bromide, 1-cyano-3-butene and phase transfer catalyst and (ii) an aqueous phase comprising a solution of the alkali metal halide and cyanide and phase transfer catalyst;
   (2) separating organic phase (i) from aqueous phase (ii) from step (1);
   (3) contacting organic phase (i) from step (2) with elemental bromine to obtain a reaction mixture comprising cyclopropylacetonitrile, cyclobutyl bromide, 4-cyano-1,2-butane dibromide and phase transfer catalyst; and (4) subjecting the reaction mixture of step (3) to fractional distillation to obtain overhead vapor products comprising cyclopropylacetonitrile and cyclobutyl bromide and a distillation base residues comprising 4-cyano-1,2-butane dibromide and phase transfer catalyst.

4. Process according to claim 3 wherein Step 1 comprises contacting a reactant mixture comprising, based on the total weight of cyclopropylmethyl bromide, cyclobutyl bromide and bromobutene=100%, about 40 to 60% cyclopropylmethyl bromide, about 30 to 50% cyclobutyl bromide and about 5 to 10% bromobutene with an aqueous solution of an alkali metal cyanide at a temperature of about 350 to 55° C. in the presence of a phase transfer catalyst to obtain a reaction mixture comprising (i) an organic phase comprising cyclopropylacetonitrile, cyclobutyl bromide, 1-cyano-3-butene and phase transfer catalyst and (ii) an aqueous phase comprising a solution of the alkali metal halide and cyanide and phase transfer catalyst; wherein the aqueous solution of an alkali metal cyanide contains about 1.2 to 3 moles alkali metal cyanide per mole of each of cyclopropylmethyl bromide, cyclobutyl bromide and bromobutene.

5. The process according to claim 3 wherein Step 1 comprises contacting a reactant mixture comprising, based on the total weight of cyclopropylmethyl bromide, cyclobutyl bromide and bromobutene=100%, about 40 to 60% cyclopropylmethyl bromide, about 30 to 50% cyclobutyl bromide and about 5 to 10% bromobutene with an aqueous solution of an alkali metal cyanide selected from sodium or potassium cyanide at a temperature of about 35 to 55° C. in the presence of about 7 to 17 weight percent, based on the total weight of cyclopropylmethyl bromide, cyclobutyl bromide and bromobutene, of a phase transfer catalyst to obtain a reaction mixture comprising (i) an organic phase comprising cyclopropylacetonitrile, cyclobutyl bromide, 1-cyano-3-butene and phase transfer catalyst and (ii) an aqueous phase comprising a solution of the alkali metal halide and cyanide and phase transfer catalyst; wherein the aqueous solution of sodium or potassium cyanide contains about 1.2 to 3 moles sodium or potassium cyanide per mole of each of cyclopropylmethyl bromide, cyclobutyl bromide and bromobutene and the phase transfer catalyst contains about 12 to 36 carbon atoms and has the general formula:

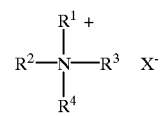

wherein $R^1$, $R^2$, $R^3$, and $R^4$ are the same or different and are selected from alkyl of up to 18 carbon atoms and benzyl and X is an anion; and
   Step 3 comprises contacting organic phase (i) from step 2 with elemental bromine at a temperature of about −10° to 30° C. to obtain a reaction mixture comprising cyclopropylacetonitrile, cyclobutyl halide, 4-cyano-1,2-butane dibromide and phase transfer catalyst wherein about 1 to 1.2 moles of bromine per mole of 1-cyano-3-butene present is added to the organic phase of step (i) from step 2.

* * * * *